United States Patent
Eizenhöfer

(10) Patent No.: US 6,915,697 B2
(45) Date of Patent: Jul. 12, 2005

(54) TESTING AND MONITORING OF A SHOCK WAVE OR PRESSURE WAVE SOURCE

(75) Inventor: Harald Eizenhöfer, Seefeld (DE)

(73) Assignee: Dornier MedTech Systems GmbH, Wessling (DE)

(*) Notice: Subject to any disclaimer, the term of this patent is extended or adjusted under 35 U.S.C. 154(b) by 0 days.

(21) Appl. No.: 10/872,140

(22) Filed: Jun. 18, 2004

(65) Prior Publication Data

US 2005/0016285 A1 Jan. 27, 2005

Related U.S. Application Data

(63) Continuation of application No. PCT/DE02/04638, filed on Dec. 18, 2002.

(30) Foreign Application Priority Data

Dec. 19, 2001 (DE) .......................................... 101 62 595

(51) Int. Cl.$^7$ ............................................... G01N 9/18
(52) U.S. Cl. ...................... 73/654; 73/11.05; 73/12.04; 73/659
(58) Field of Search .......................... 73/654, 657, 659, 73/11.04, 11.05, 12.04, 12.01

(56) References Cited

U.S. PATENT DOCUMENTS

| | | | | |
|---|---|---|---|---|
| 2,859,726 A | * | 11/1958 | Bouyoncos et al. | 116/137 A |
| 3,056,312 A | * | 10/1962 | Aldikacti et al. | 74/574 |
| 3,505,880 A | * | 4/1970 | Riordan | 73/514.11 |
| 3,555,880 A | * | 1/1971 | Menius, Jr. et al. | 73/32 A |
| 4,546,960 A | * | 10/1985 | Abrams et al. | 267/136 |
| 6,135,357 A | * | 10/2000 | Herrin et al. | 239/4 |

* cited by examiner

Primary Examiner—Hezron Williams
Assistant Examiner—Jacques M. Saint-Surin
(74) Attorney, Agent, or Firm—King & Spalding LLP

(57) ABSTRACT

A device for the testing and monitoring of the function of a shock wave or pressure wave source is provided. The testing and monitoring device is characterized in that a passive non-linear transmission element transforms very short shock wave pulses received by it, the shock wave pulses typically having pulse durations lasting a few microseconds, into a considerably lower frequency range, whose oscillations are then sensed and evaluated.

14 Claims, 2 Drawing Sheets

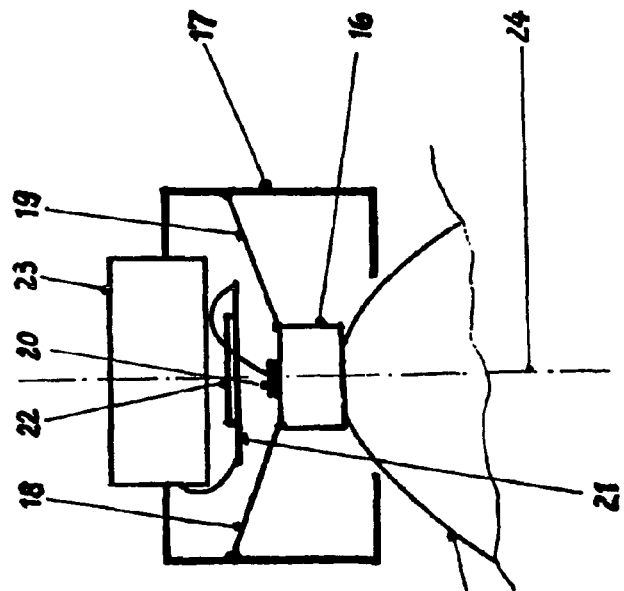
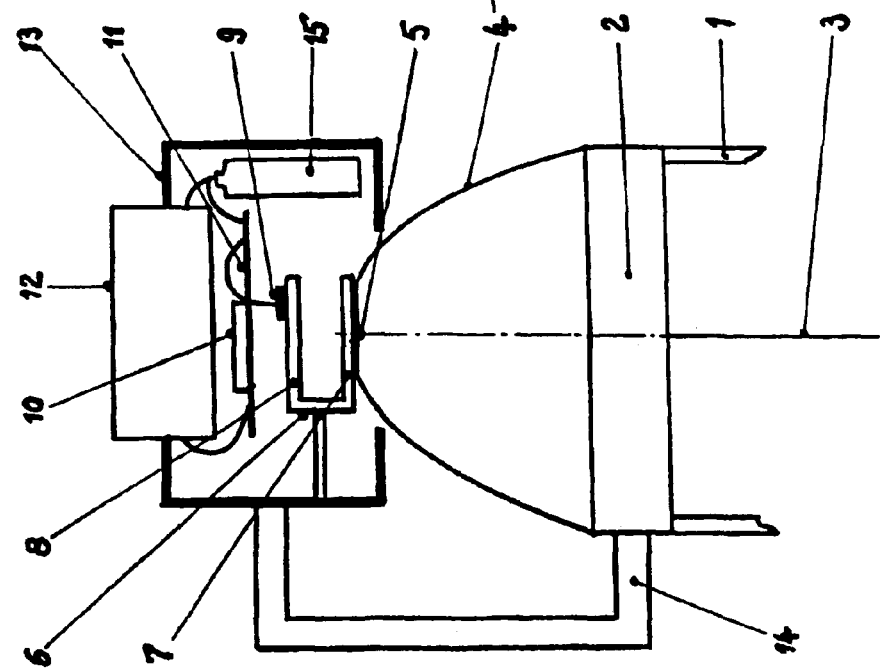

TESTING AND MONITORING OF A SHOCK WAVE OR PRESSURE WAVE SOURCE

CROSS-REFERENCE TO RELATED APPLICATION

This application is a continuation, under 35 U.S.C. § 365(a), of the co-pending PCT patent application having International Application No. PCT/DE02/04638, having International Filing Date 18 Dec. 2002 (18, Dec. 2002), which claims priority to German Patent Application No. 101 62 595.2, filed on Dec. 19, 2001, and which is incorporated herein by reference. Additionally, this application claims priority under 35 U.S.C. § 119(a) to German Patent Application No. 101 62 595.2, filed on Dec. 19, 2001, which is incorporated herein by reference.

FIELD OF THE INVENTION

The present invention relates to the testing and monitoring of the function of a shock wave or pressure wave source like that used, for example, within the framework of electromagnetic shock wave lithotripsy.

BACKGROUND OF THE INVENTION

For quality assurance and function control of shock wave or pressure wave sources used in the medical field, hereinafter only briefly called shock wave sources, end test and service technicians carry out pressure measurements with the help of piezoelectric sensors and also crushing tests with synthetic stones.

Both test methods have a number of inherent drawbacks that shall here be mentioned and commented only by way of example. Both test methods require a test vessel filled with water, the gas content within the water being subjected to a permanent strict control. Moreover, the piezoelectric measuring technique presupposes comprehensive experience in handling oscilloscopes. Furthermore, the quality of the plaster balls used in crushing tests has not always the same level to be expected; so-called soaking times have to be waited for and strictly observed.

SUMMARY OF THE INVENTION

It is an objective of the present invention to provide a much simpler, robust and reliable measuring device for testing and monitoring the above-mentioned shock wave source to avoid the drawbacks as outlined. This measuring device should also be easy to operate and should rarely pose any problems with respect to maintenance. Moreover, for the above-mentioned purpose, a monitoring device is provided that remains permanently on the corresponding devices and can serve to monitor the devices constantly, also during their use.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following and more particular description of the invention which is illustrated in the accompanying drawings, wherein:

FIG. 1 shows a shock wave source with a coupling bellows which is filled with a suitable fluid, such as water, and whose front side has positioned thereon a resonating construction similar to a tuning fork, which has a lower leg resting on the coupling bellows.

FIG. 2 shows a coupling bellows whose front side contacts a cylindrical absorber in axial symmetry.

DETAILED DESCRIPTION OF THE INVENTION

Figure 3:
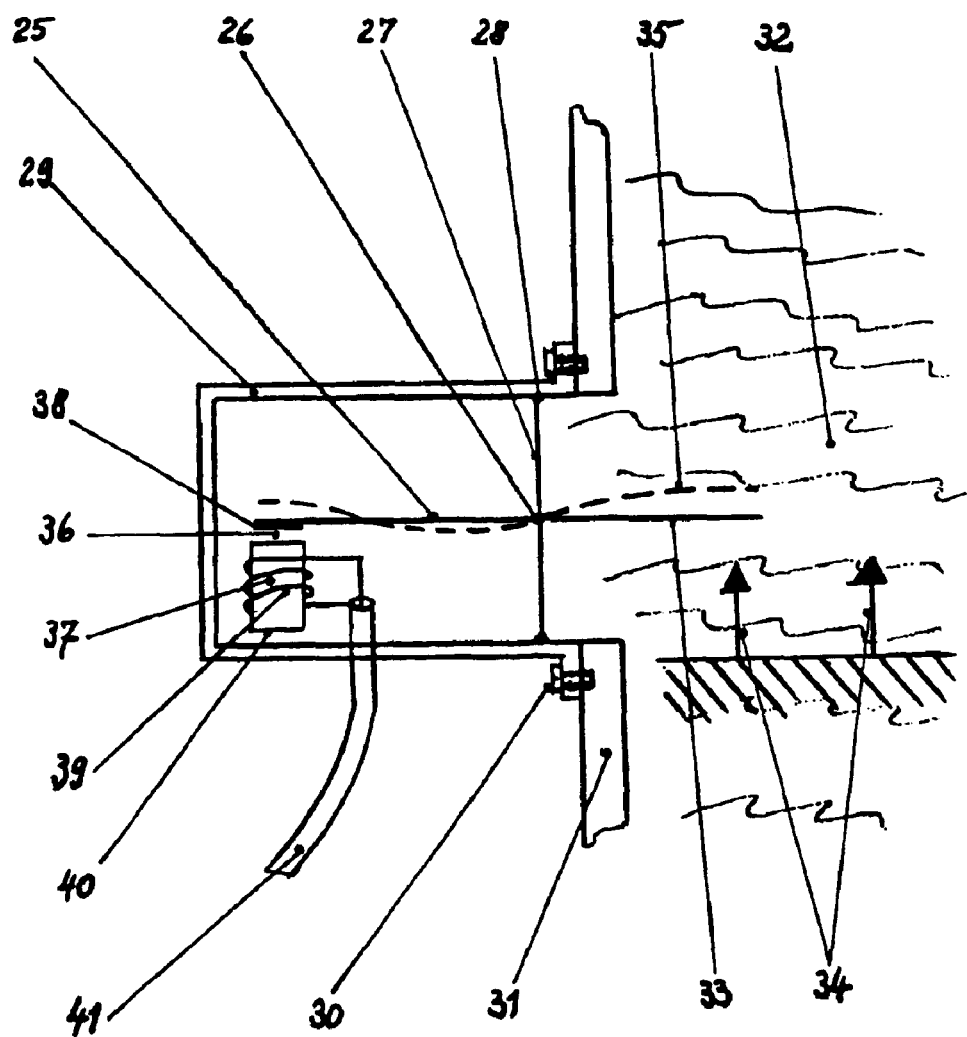
FIG. 3 shows, as an oscillating or resonating construction, a special steel wire which within the scope of the measuring means of the invention projects with part of its length into the shock wave path.

Exemplary embodiments of the present invention will be described hereinafter with reference to the drawings wherein like elements and structures are indicated by like reference numbers. In accordance with such exemplary embodiments, a testing and monitoring device includes a passive non-linear transmission element that transforms the very short shock wave pulses received by it, which typically have pulse durations of a few microseconds, into a much lower frequency range, for example, of about 0.1 to 1 kHz, whose oscillations are then sensed and evaluated. The passive non-linear transmission element showing the characteristic of spectral conversion may virtually be of any oscillating construction. For illustrative purposes, it is possible to talk about a bell or a tuning fork that, being excited by a pulse, carries out natural oscillations.

The analytical part of the sensor system to be used within the scope of the invention includes drawing the right conclusions as to the magnitude of the excitation pulse from the recorded oscillation behavior of the transmission element. To this end, the "sound volume", the spectral composition of the oscillations, the decay behavior of individual spectral portions, etc., can be evaluated individually or in combination.

The sensor to be mounted on the transmission element may preferably be an inexpensive airbag-release acceleration sensor when the accelerations are to be measured by structures of the construction. For the measurement of the sound pressure, a corresponding microphone would suffice. In the present context, however, the above-mentioned airbag sensors are more advantageous, where, in contrast to microphones, signal processing, signal filtering, and, at least partly, even a digital current interface are integrated on a chip. Therefore, the overall efforts ranging from the downstream electronic system to the display of the measured variable can be expected to be small in the case of airbag sensors. The great insensitivity to electromagnetic interference which can be expected and is always found in the case of shock wave sources operated with electrical pulses in the megawatt range is also in support of the highly integrated sensor chip with integrated high-pass filter.

In a further embodiment of the invention a medium with a high absorption of the incoming acoustic pulse may serve as a passive non-linear transmission element. In this instance, an illustrative example is a sand bag which, when being shot at by a projectile, fully decelerates the same. Due to the pulse maintenance, the pulse of the incoming acoustic shock wave can be measured via the acceleration of the absorber.

The sensor can here also be mounted directly on the absorber. To achieve high acceleration values, i.e. a good signal-to-noise ratio, the total mass of absorber/sensor must be kept small. This restriction is not required in a resonating construction because the mass of sensor/chip can barely influence the oscillating behavior of the construction or can even be taken into account in the design of the resonating construction.

Special developments within the scope of the invention can be gathered from the following description of the figures and from the patent claims. One important advantage of the invention is that low-frequency oscillations can be recorded much more easily with commercial airbag release sensors than the high-frequency direct shock wave pulses.

FIG. 1 shows a therapy head 1, e.g. for performing extracorporeal lithotripsy, which includes, inter alia, a shock wave source 2. Said source is connected via a line 3 to an electrical supply unit, which is not shown separately. At the patient's side, the shock wave source 2 is completed with a water-filled coupling bellows 4 which during therapy is in contact with the corresponding body part of the patient, i.e., via which the shock waves are normally introduced into the patient's body without the measuring means according to FIGS. 1 and 2.

For the inventive measurement, monitoring and/or control of the shock wave source 2 the front side 5 of the coupling bellows 4 is in close contact with a resonating construction in the form of a tuning fork 6 lying in such a manner that the lower leg 7 of the tuning fork 6 touches the coupling bellows 4 on the front side while the upper free leg 8 comprises a fixedly mounted acceleration sensor 9, preferably at its free end. Said sensor is connected to an electronic printed circuit board 11 carrying various chips 10. A display 12 which is in communication with the printed circuit board 11 shows the measurement results to the viewer on the basis of the signals recorded by the acceleration sensor 9.

A protective housing 13 is fixedly connected by means of a mounting 14, but detachably to the therapy head 1. Inside the protective housing 13, a battery 15 may be additionally accommodated, which supplies the electronic system of the printed circuit board 11, the acceleration sensor 9, and the display 12 with voltage.

FIG. 2 shows the same test object as FIG. 1 with respect to reference numerals 1 to 4. The measuring means is also virtually identical with respect to reference numerals 9 to 15. In contrast to FIG. 1, the resonating construction is an absorber 16 in the measuring means according to FIG. 2. Said absorber is suspended inside a protective housing 17 from threads or springs 18 and 19.

An acceleration sensor 20 which is connected to an electronic printed circuit board 21 is mounted on the absorber 16. Apart from this, the electronic measuring means is identical with that of FIG. 1. The display has reference numeral 23 in this instance. Chips 22 are provided on the printed circuit board 21. The longitudinal axis of the therapy head bears reference numeral 24.

FIG. 3 shows a measuring means within the scope of the invention that differs essentially from the solutions provided in FIGS. 1 and 2 in that the resonating construction is not exclusively resting from the outside on the therapy head, but partly projects into said head, namely preferably into the fluid between the electromagnetic shock wave source and the acoustic lens. The resonating construction of the invention according to FIG. 3 is a special steel wire 25 that is hardened, if possible, and in its passage 26 through a special steel membrane 27 is welded to the latter with a quality that is as high as possible. The membrane 27, in turn, is tightly welded to a housing 29 in the surrounding portion 28, also with a quality that is as high as possible. The housing 29 is tightly connected by means of screws 30 to the housing 31 of a therapy head 32.

When the part 33 of the wire 25 that projects into the therapy head 32 is subjected by a shock wave 34 to a pulse, the wire 25 starts to oscillate. The broken line 35 is meant to illustrate said oscillation on an exaggerated scale.

When the oscillations of the wire 25 are sensed with a so-called pick-up coil 37, as shown in FIG. 3, the wire 25 in the measurement area 36 must then show some kind of permeability that is much greater than 1. This is ensured by a correspondingly ferritic metal part 38 which must be fastened to the wire 25 in the measurement area 36. The signal sensor 37 consists of a coil 39 and of a permanent magnet 40. The recorded measured values may be supplied via a line 41 to an electronic processing means for displaying the measurement results. Further sensing methods, particularly of an optical kind, are possible.

While the invention has been described with respect to the foregoing exemplary embodiments, it will be apparent to those skilled in the art that various modifications, variations and improvements of the invention can be made in light of the above teachings and within the purview of the appended claims without departing from the spirit and intended scope of the invention. In regard to the foregoing description of the exemplary embodiments of the invention, areas which are known to those of ordinary skill in the art have not been described in detail in order to facilitate a clear and concise description of the invention. Accordingly, it should be understood that the invention is not to be limited by the specific exemplary embodiments, but only by the scope of the appended claims.

What is claimed is:

1. A device for testing and monitoring shock wave or pressure wave sources, comprising a passive, non-linear oscillating or resonating construction excitable by a shock wave or pressure wave such that said construction transforms a very short shock wave or pressure wave pulses having pulse durations of a few microseconds into a substantially lower frequency range so that the oscillations of said construction can be recorded and analyzed by an electronic means and can be read as measurement results on a display.

2. The device of claim 1, wherein said substantially lower frequency range is 0.1 kHz to 1 kHz.

3. The device of claim 1, wherein said oscillating or resonating construction has a basic form of a tuning fork of which one leg is in a close planar contact with a front side of a coupling bellows of a shock wave or pressure wave source that is filled with a suitable fluid and of which another leg of said tuning fork is provided at its free end with an acceleration sensor which transmits the oscillation signals received by it to one or more chips for processing, said chips being arranged on an electronic printed circuit board that is connectable to said display for visualizing measurement results.

4. The device of claim 1, wherein said oscillating or resonating construction is an absorber with a front side in close contact with a coupling bellows and said construction has fastened thereto an acceleration sensor which transmits recorded signals to said electronic means to be analyzed or processed while said absorber is suspended in a protective housing which covers a monitoring means from threads or springs as a seismic mass.

5. The device of claim 3, wherein said oscillating or resonating construction is an absorber with a front side in close contact with said coupling bellows and said construction has fastened thereto an acceleration sensor which transmits recorded signals to said electronic means to be analyzed or processed while said absorber is suspended in a protective housing which covers a monitoring means from threads or springs as a seismic mass.

6. The device of claim 1, wherein said oscillating or resonating construction is a hardened steel wire which is welded in its passage through a steel membrane to said membrane, said membrane being welded in a surrounding portion to a housing which is tightly connected via screws to a housing of a therapy head, wherein an inwardly oriented part of said steel wire projects into a liquid coupling medium of said therapy head such that said steel wire is excitable by said shock wave to oscillate, wherein signals can be picked up in a measurement area by means of a signal sensor in the form of a coil and a permanent magnet, said signals being supplied via a line to an electronic processing means for display of the measurement results.

7. The device according to claim 6, wherein said signals are picked up in accordance with a principle of electromagnetic induction according to the change in time of a magnetic flux through said coil.

8. The device of claim 1, wherein said oscillations are sensed optically.

9. The device of claim 2, wherein said oscillations are sensed optically.

10. The device of claim 3, wherein said oscillation signals are sensed optically.

11. The device of claim 4, wherein said recorded signals are sensed optically.

12. The device of claim 5, wherein said recorded signals are sensed optically.

13. The device of claim 6, wherein said signals are sensed optically.

14. The device of claim 7, wherein said signals are sensed optically.

* * * * *